United States Patent [19]
Palti

[11] Patent Number: 5,474,552
[45] Date of Patent: Dec. 12, 1995

[54] IMPLANTABLE DRUG DELIVERY PUMP

[75] Inventor: Yoram Palti, Haifa, Israel

[73] Assignee: CB-Carmel Biotechnology Ltd., Israel

[21] Appl. No.: 266,736

[22] Filed: Jun. 27, 1994

[51] Int. Cl.$^6$ ................................................. A61M 5/00
[52] U.S. Cl. ................................................. 604/67
[58] Field of Search ................................. 604/65, 66, 67, 604/30–34, 50, 251, 253, 890.1, 891.1, 892.1, 51, 52, 53, 246–249; 128/DIG. 13, DIG. 12

[56] References Cited

U.S. PATENT DOCUMENTS

| | | | |
|---|---|---|---|
| 4,055,175 | 10/1977 | Clemens et al. | 604/65 |
| 4,282,872 | 8/1981 | Franetzki et al. | 604/67 |
| 4,731,051 | 3/1988 | Fischell | 604/50 |
| 4,822,336 | 4/1989 | Di Traglia | 604/50 |
| 4,925,444 | 5/1990 | Orkin et al. | 604/80 |
| 5,101,814 | 4/1992 | Palti . | |
| 5,104,374 | 4/1992 | Bishko et al. | 604/31 |
| 5,190,041 | 3/1994 | Palti . | |
| 5,190,522 | 3/1994 | Wojcicki et al. | 604/31 |
| 5,298,021 | 3/1994 | Sherar | 604/50 |

OTHER PUBLICATIONS

Meize-Grochowski, A. R. "Health locus of control and glycosylated haemoglobin concentration of implantable insulin pump recipients in Austria." *J Adv Nurs* 15 (1990): 804–807.

Ranade, V. V. "Drug delivery systems. 4. Implants in drug delivery. [Review]." *J. Clin Pharmacol* 30 (1990): 871–889.

Saudek, C. D., et al., "The Programmable implantable medication system (PIMS): design features and pre-clinical trials. [Review]." *Horm Metab Res* 22 (1990): 201–206.

Selam, J. L. "Implantable insulin pumps: a major piece of computerized diabetic therapy. [Review]." *Horm Metab Res Suppl* 24 (1990): 144–154.

Saudek, C. D., "Future developments in insulin delivery systems." *Diabetes Care* 16 (1993): 122–132.

Saudek, C. D. "Implantable insulin infusion pumps." *The Endocrinologist* 3 (1993): 15–20.

Hildebrandt, G., et al., "Results of continuous long-term intravenous application of octreotide via an implantable pump system in acromegaly resistant to operative and X-ray therapy." *Acta Neurochir (Wein)* 117 (1992): 160–165.

Jeandidier, N., et al., "Comparison of intraperitoneal insulin infusion (using implantable pump) and subcutaneous insulin administration: preliminary results of a crossover study." *Transplant Proc* 24 (1992). 948–949.

Saudek, C. D. "Implantable insulin pumps: a current look." *Diabetes Research & Clinical Practive* (1990): 109–114.

Saudek, C. D., et al. "The Dept. of Veterans Affairs implanted insulin pump study." *Diabetes Care* (1992): 567–570.

Selam, J. L. and G. Slama. "[Insulin administration systems; possibilities and difficulties]. [Review][French]." *Presse Med* 21 (1992): 1575–1580.

Selam, J. L., et al., "Clinical trial of programmable implantable insulin pump for type 1 diabetes." *Diabetes Care* 15 (1992): 877–885.

Waxman, K., et al. "Implantable programmable insulin pumps for the treatment of diabetes." *Arch Surg.* 127 (1992): 1032–6; discussion 1036–7.

Primary Examiner—C. Fred Rosenbaum
Assistant Examiner—Manuel Mendez
Attorney, Agent, or Firm—Bryan Cave; David M. Klein

[57] ABSTRACT

A method and apparatus for maintaining the concentration of glucose in a person, animal or tissue within a predetermined range is disclosed. An implanted sensor of living cells produces a detectable electrical signal which varies with the concentration of glucose. A controller detects the electrical signal produced by the sensor and determines if the concentration of glucose is within the predetermined range. If the glucose is too low or too high, the controller activates a pump causing either glucose or glucagon, or insulin to be delivered to the person until the glucose level is within the predetermined range. A separate pump for delivering each of the glucose and insulin may be used, or a single pump which is switchable between them may be used. The system may be adapted to maintain other constituents or conditions within a predetermined range by changing the sensor in use, and by using agents and counteragents appropriate to the condition or constituent level being monitored.

17 Claims, 2 Drawing Sheets

IMPLANTABLE DRUG DELIVERY PUMP

BACKGROUND OF THE INVENTION

1. Field of the Invention

The present invention relates to a method and apparatus for continuously detecting the level of glucose in a person, and for automatically delivering glucose or glucagon, and insulin to the person to maintain the glucose level in a desired range. The invention also relates to a method and apparatus for regulating other conditions or constituent levels in a person, tissue, or animal by continuously sensing the condition or constituent levels and delivering an agent and counteragent for maintaining the condition or constituent levels in a desired range.

2. Description of the Related Art

One of the more advanced methods of drug delivery is one in which the amount of a drug delivered is controlled by a sensor. The sensor reads, for example, the concentration of a constituent in the blood or tissue, or the magnitude of the results of a previous drug delivery, and alters the quantity or rate of delivery of a drug for altering the detected constituent concentration. For example, in a system for insulin delivery, the sensor can read the blood glucose level and vary the insulin delivery amount or rate accordingly.

At present there are very few sensors available which can function in this manner. One such sensor is disclosed in commonly owned U.S. Pat. Nos. 5,101,814 and 5,190,041, and U.S. patent application Ser. No. 08/077,893, the contents of which are incorporated herein by reference. This sensor comprises a mass of living cells which are sensitive to a particular constituent, preferably glucose. The cells are encapsulated in a biocompatible semi-permeable membrane and generate a detectable electrical signal which varies with the concentration of the constituent in the medium that surrounds the cells or capsule.

Most existing feedback controlled drug delivery systems suffer from the inability to lower the drug level, or its efficacy, once delivered. Thus, any overdose cannot be counteracted and one has to wait until natural metabolism and excretion lower the level of the agent administered.

There are however cases where a counteragent is available. For example, in the case of insulin hormone delivery, if an overdose is sensed by the sensor in the form of a too low glucose level, the situation can be corrected by delivery of glucose, or the hormone glucagon, etc.

It is therefore an object of the present invention to improve sensor controlled delivery systems by providing the capability to automatically deliver either a chemical agent or counteragent based on continuous sensor readings to maintain the level of a constituent or condition, for example blood pressure, within a desired range.

SUMMARY OF THE INVENTION

The present invention is a method and apparatus for maintaining the concentration of a constituent in a person, tissue, animal, etc. within a predetermined range or to follow specified programmed changes. Although the constituent preferably glucose, it may be any constituent or condition which can be regulated by delivery of an agent to increase or decrease the constituent level or condition, and a counteragent to decrease or increase the constituent level or condition.

A sensor, preferably of the type which produces a detectable electrical signal which varies with the concentration of the constituent or the existence of the condition is implanted in the person. A controller detects the electrical signal produced by the sensor and determines if the concentration of the constituent or the condition is within a predetermined range at a given time. If the level or condition is too low or too high, the controller activates a pump causing either agent or counteragent to be delivered to the person until the constituent or condition is within the predetermined range, or, if the body response is slower than the delivery, until the predicted constituent or condition level is within a required range.

In a preferred embodiment, the sensor is an implantable mass of living cells which is sensitive to glucose levels and the delivered drugs are glucose or glucagon and insulin. A separate pump for delivering each of the agent and counteragent may be used, or a single pump which is switchable between the agent and counteragent may be used.

DESCRIPTION OF THE PREFERRED EMBODIMENT

Figure 1:
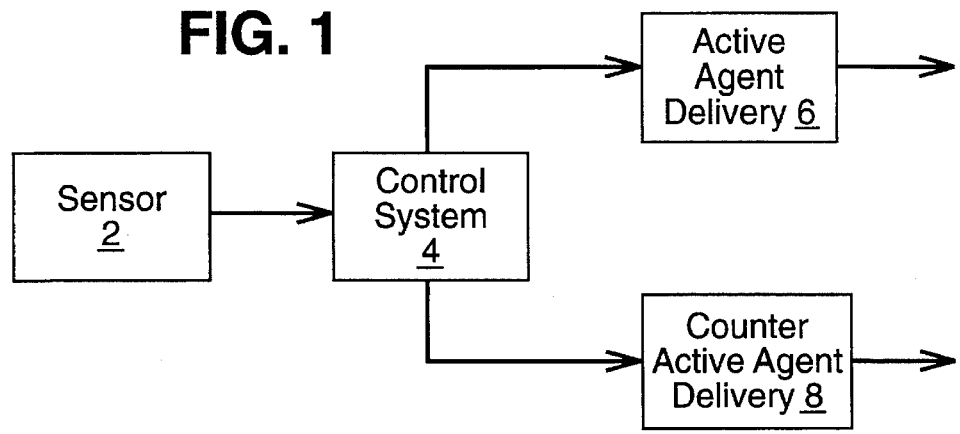
FIG. 1 shows a block diagram of the drug delivery system of the present invention.
Figure 2:
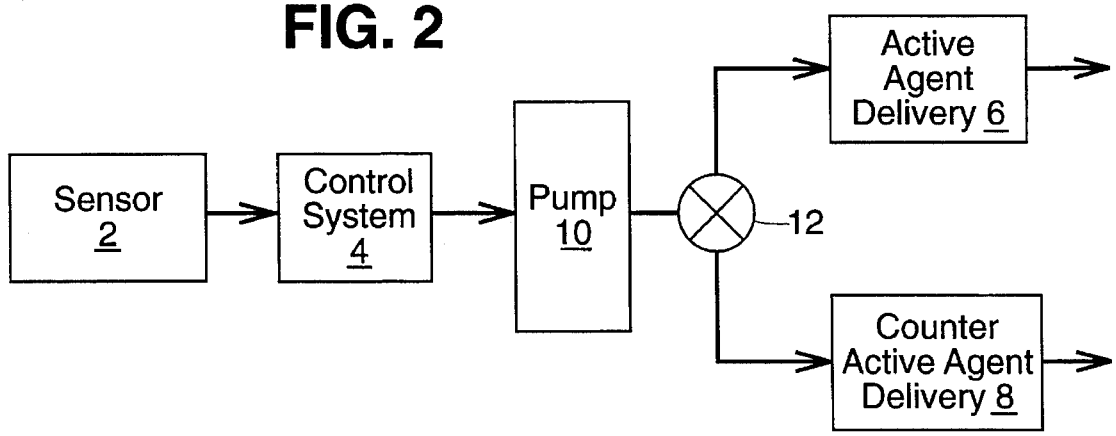
FIG. 2 shows a block diagram of an alternative embodiment of the drug delivery system of the present invention.

The present invention is a drug delivery system in which a condition or constituent level in a person, tissue or animal is continuously monitored, and maintained within a predetermined range. As shown in FIG. 1, the invention includes a sensor 2, a controller or control system 4, an agent delivery system 6, and a counteragent delivery system 8. In an alternative embodiment, as shown in FIG. 2, a separate pump 10 is provided for delivering each of the agent and counteragent. In the embodiment shown in FIG. 1, the pump is incorporated in the agent and counteragent delivery systems 6 and 8.

Sensor 2 is implanted in the body tissue or fluids of a person and generates an electrical or other detectable signal in response to the presence of constituents to which the sensor is sensitive, or other conditions, i.e. temperature, pressure, etc. For example, such a sensor might be of the type disclosed in commonly owned U.S. Pat. Nos. 5,101,814 and 5,190,041, and U.S. patent application Ser. No. 08/077, 893. In these sensors, living cells which generate a varying electrical signal in the presence of constituents to which the cells are sensitive are encapsulated in a biocompatible semi-permeable membrane, and the electrical activity of the living cells is measured. The sensors may be sensitive to glucose levels, for example, and generate an electrical signal which varies with the concentration of glucose in the medium surrounding the sensor 2. The sensors may also generate other non-electrical signals, i.e. optical, chemical, etc. provided that the signals are detectable. Of course, it is foreseen that any type of appropriate sensor, whether implanted or not, may be used in the present system.

Controller 4 receives the electrical output of sensor 2, and determines whether the level of the constituent or condition is too high or too low, and thus requires administration of an agent or counteragent to raise or lower the level. The controller then regulates the delivery of agent and counteragent to maintain the constituent level or condition to which the sensor is sensitive within a predetermined range, or to follow specified programmed changes. The controller 4, pump 10 and the delivery systems 6 and 8 are preferably implanted within the body, with the sensor 2 connected to the controller using conventional leads, with the agents and counteragents being delivered to the person by any means known in the art. In the alternative, any combination of the controller 4, pump 10 delivery systems 6 and 8, as well as a supply of the agent and counteragent, may be located outside the body with the sensor connected to the controller using conventional electrodes or electrical pickups, with agent and counteragent being delivered to the person by tubing of the type known in the art. If appropriate, sensor 2 may also be located outside of the body.

Although the preferred embodiment will be described in detail with respect to the delivery of a soluble drug, the agent(s) to be delivered can be any type of drug, hormone, pH buffering solution, living cells or other agents in suspension, or any other biologically active material, etc. depending upon the type of sensor 2 in use and the constituent or condition being monitored.

The drug delivery system must be able to deliver a controlled volume or a controlled rate of the agent or counteragent into the appropriate body fluid, cavity or tissue, i.e., blood, peritoneal cavity, subcutaneous tissue, etc. In a preferred embodiment, as shown in FIG. 2, the delivery of the drug is done by an electrically controlled pump 10. The pump 10 may be of any conventionally known type, including a piston or piston equivalent (fluid or gas) driven pump, a peristaltic pump, centrifugal pump, etc. In the alternative, the drug delivery may be carried out by controlled diffusion, by an electric current that carries a charged agent, by charged molecules or particles, by magnetic particles, etc.

Figure 3:
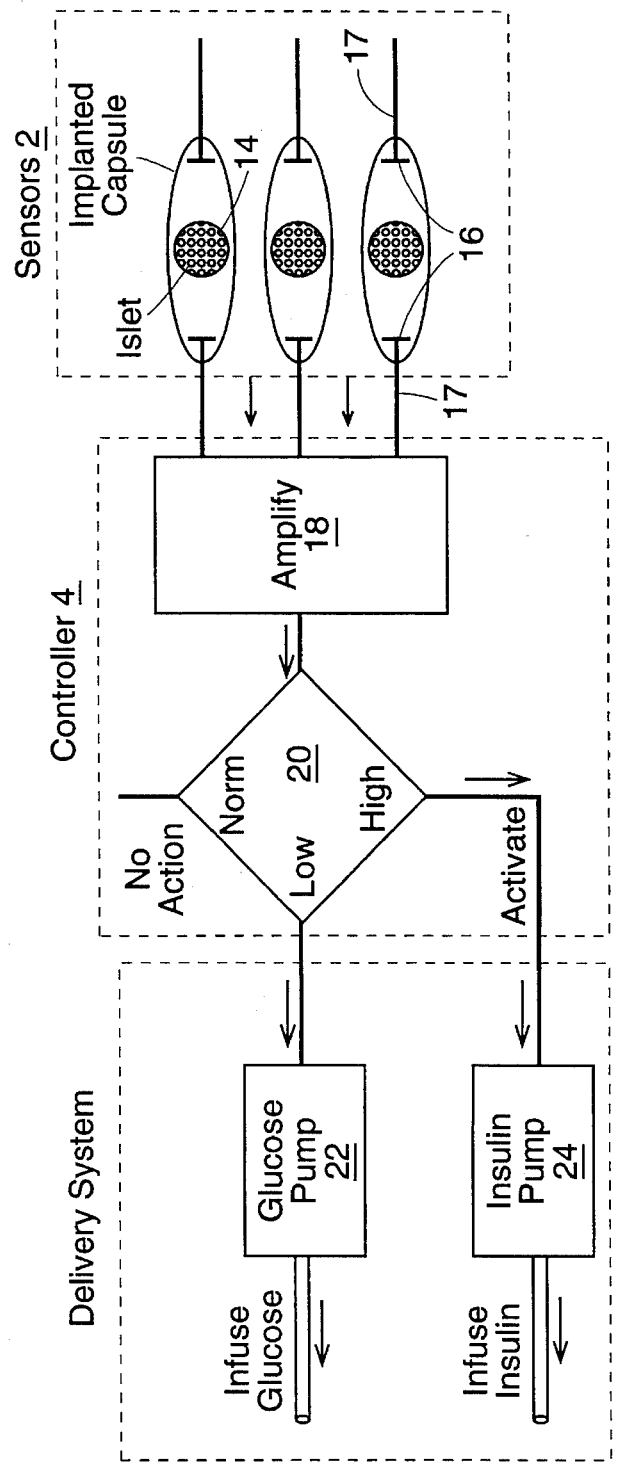
FIG. 3 shows a schematic diagram of another alternative embodiment of the drug delivery system of the present invention.
Figure 4:
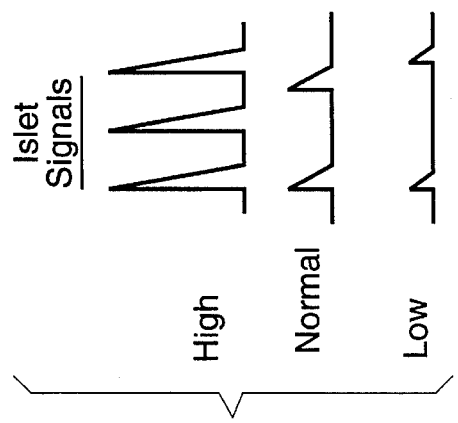
FIG. 4 shows sample electrical signals generated by an implanted cell mass.

As shown in FIG. 3, the present invention shall now be described with respect to an implanted insulin-glucose or insulin-glucagon delivery system. The glucose sensors 2, are of the type disclosed in the aforementioned U.S. Pat. Nos. 5,101,814 and 5,190,041, and U.S. patent application Ser. No. 08/077,893. Each sensor comprises a mass of living cells 14 which are sensitive to glucose levels and which generate an electrical signal which varies with the concentration of glucose in the medium surrounding the cells, as shown in simplified form in FIG. 4. The mass of cells 14 may be contained in a capsule of the type disclosed in the commonly owned co-pending U.S. Patent application entitled "IMPLANTABLE CAPSULE FOR ENHANCING CELL ELECTRIC SIGNALS", filed concurrently herewith The sensors 2 are implanted in a body cavity where the glucose concentration is representative of the overall blood glucose concentration in the person. The sensors 2 continuously sense the glucose concentration by means of electrodes 16 and transmit this information to the control system 4 by means of leads 17. Electrodes 16 may be of any type known to those skilled in the art.

The control system 4 includes an amplifier 18 which receives and amplifies the signals from the sensors 2. The controller 4 processes the inputs for determining the glucose levels in the person. The controller may further process the sensor readings to compensate for concentration reduction and delays due to diffusion, etc. Using the glucose readings and a drug activation algorithm 20, the controller 4 determines whether drug delivery is appropriate and, if so, generates control signals to cause the delivery of glucose via glucose pump 22 or the delivery of insulin via insulin pump 24.

The controller 4 can be of any type for performing the functions set forth herein. For example, controller 4 may be a modified On-Off type or a Proportional Control type. In the first case, if the controller 4 determines that the glucose concentration exceeds a specified criterion at the given time, insulin pump 24 is activated at predetermined rates for specified durations so as to appropriately lower the blood glucose levels. The pumping mechanism itself may include either a dedicated pump for each agent, as shown in FIG. 3, or a single pump which can pump more than one agent, as shown in FIG. 2. In the single pump embodiment, the controller 4 activates the pump 10 and couples it with the appropriate delivery system, i.e., the glucose system or the insulin system. The coupling 12 may be a mechanical gear that switches the pump cylinder, for example, or a valve that allows the correct agent to flow once the system is pressurized, or any other conventionally known coupling. When the sensors 2 and controller 4 detect a normal glucose level, the pump 10 is stopped or switched to a basal level or another predetermined level which indicates that the level will approach the normal range without any further intervention.

When the sensors 2 and controller 4 detect a glucose level below a certain level, the glucose delivery system 22 is activated. This may be done either by activating the appropriate pump, or by switching the single pump to deliver glucose. If desired, the control system 4 can activate a glucagon delivery system. Glucagon is a hormone that counteracts many of the effects of insulin and increases blood glucose levels.

If the controller 4 is of the proportional type, the control algorithm causes the delivery system to output an amount or delivery rate of the agents or counteragents in proportion to the detected level of the constituent being detected.

If desired, the present system can be modified so that more than two related chemicals may be delivered. For example, the system may be a three agent delivery system, wherein the controller can activate and regulate the delivery of insulin, glucose, and glucagon, each at the appropriate rate and amount.

Although the present invention has been described in detail with respect to certain embodiments and examples, variations and modifications exist which are within the scope of the present invention as defined in the following claims.

I claim:

1. An apparatus for regulating a condition or concentration of a constituent in a person, animal, or living tissue the constituent or condition being increasable by delivery of an agent to the person, animal or living tissue, and decreasable by delivery of a counteragent to the person, animal or living tissue;

the apparatus comprising:
a sensor implanted in the person or tissue, the sensor producing a detectable signal which varies with the concentration of the constituent or the existence of the condition in a medium surrounding the sensor;
a source of agent;
a source of counteragent;
delivery means for controllably delivering each of the agent and counteragent to the person or tissue; and
a controller for detecting the signal produced by the sensor and for determining if the concentration of the constituent or the condition is within a predetermined range, the controller causing the delivery means to selectively deliver agent or counteragent to maintain the concentration of the constituent or the condition within the predetermined range.

2. The apparatus according to claim 1 wherein the sensor is an implantable mass of living cells.

3. The apparatus according to claim 2 wherein the constituent is glucose and the implantable mass of cells is sensitive to glucose levels.

4. The apparatus according to claim 3 wherein the agent is glucose and the counteragent is insulin.

5. The apparatus according to claim 3 wherein the agent is glucagon and the counteragent is insulin.

6. The apparatus according to claim 3 wherein the delivery means comprises:

a pump for the glucose; and a pump for the insulin.

7. The apparatus according to claim 3 wherein the delivery means comprises:

a pump; and a coupling for switching the pump between the source of glucose and the source of insulin.

8. The apparatus according to claim 1 wherein the delivery means comprises:

a pump for the agent; and a pump for the counteragent.

9. The apparatus according to claim 1 wherein the delivery means comprises:

a pump; and a coupling for switching the pump between the source of agent and the source of counteragent.

10. A method for maintaining a condition or concentration of a constituent in a person, animal or other living tissue within a predetermined range, the constituent or condition being increasable by delivery of an agent to the person, animal or living tissue and decreasable by delivery of a counteragent to the person, animal or living tissue;

the method comprising:

implanting a sensor in the person or tissue, the sensor producing a detectable signal which varies with the concentration of the constituent or the existence of the condition in a medium surrounding the sensor;

providing a source of agent;

providing a source of counteragent;

detecting the signal produced by the sensor and determining if the concentration of the constituent or the condition is within the predetermined range; and selectively and controllably delivering the agent or counteragent to the person, animal or tissue to maintain the concentration of the constituent or the condition within the predetermined range.

11. The method according to claim 10 wherein the sensor is an implantable mass of living cells.

12. The method according to claim 11 wherein the constituent is glucose and the implantable mass of cells is sensitive to glucose levels.

13. The method according to claim 12 wherein the agent is glucose and the counteragent is insulin.

14. The method according to claim 12 wherein the agent is glucagon and the counteragent is insulin.

15. An apparatus for regulating glucose levels in a person, the apparatus comprising:

a sensor implanted in the person, the sensor comprising a mass of living cells which generate a detectable electrical signal which varies with the concentration of glucose in the person;

a source of glucose or glucagon;

a source of insulin;

at least one pump for controllably delivering the glucose or glucagon and insulin to the person; and a controller for detecting the electrical signal produced by the sensor and for determining if the glucose concentration in the person is within a predetermined range, the controller causing the pump to selectively deliver glucose or glucagon, or insulin to the person until the concentration of glucose in the person is within the predetermined range.

16. The apparatus according to claim 15 which comprises:

a pump for the glucose or glucagon; and a pump for the insulin.

17. The apparatus according to claim 15 which:

a single pump for pumping the glucose or glucagon, and insulin; and a coupling for switching the pump between the source of glucose or glucagon and the source of insulin.

* * * * *